US012390425B1

(12) United States Patent
Ding

(10) Patent No.: US 12,390,425 B1
(45) Date of Patent: Aug. 19, 2025

(54) USE OF TYROSOL AS A PHYSIOLOGICAL ENHANCER OF CREATINE AND ITS APPLICATION IN CONTINUOUS HIGH INTENSITY EXERCISE

(71) Applicant: MolTek Nutrition Co., Ltd, Nanjing (CN)

(72) Inventor: Feng Ding, Nanjing (CN)

(73) Assignee: MolTek Nutrition Co., Ltd, Nanjing (CN)

( * ) Notice: Subject to any disclaimer, the term of this patent is extended or adjusted under 35 U.S.C. 154(b) by 0 days.

(21) Appl. No.: 19/005,921

(22) Filed: Dec. 30, 2024

(30) Foreign Application Priority Data

Oct. 21, 2024 (CN) ........................ 202411472062.2

(51) Int. Cl.
*A61K 31/05* (2006.01)
*A61P 21/00* (2006.01)

(52) U.S. Cl.
CPC .............. *A61K 31/05* (2013.01); *A61P 21/00* (2018.01)

(58) Field of Classification Search
CPC ...................................................... A61K 31/05
See application file for complete search history.

(56) References Cited

U.S. PATENT DOCUMENTS

2009/0142410 A1* 6/2009 Heuer ................ H10D 30/6891 424/606
2013/0059920 A1* 3/2013 Friedel .................. A61K 31/05 514/731

FOREIGN PATENT DOCUMENTS

CN 111139194 A 5/2020
CN 113388538 A 9/2021
CN 116059223 A 5/2023

OTHER PUBLICATIONS

Zhang et al. Frontiers in Pharmacology, 2019, 10:909.*

* cited by examiner

*Primary Examiner* — Rei Tsang Shiao
(74) *Attorney, Agent, or Firm* — Nitin Kaushik

(57) ABSTRACT

The present invention discloses the use of tyrosol as an enhancer of the physiological effects of creatine and its application in continuous high-intensity exercise. The enhancement of physiological effects includes, but is not limited to, improves muscle endurance, reduces decline in muscle strength, enhances utilization of creatine by muscles, stimulation of the endurance-enhancing effects of creatine, reduces the decline of endurance levels, accelerates resynthesis of phosphocreatine, increases phosphocreatine levels, improves resistance performance, and enhances endurance exercise performance. Particularly, muscle endurance after continuous high-intensity exercise does not decrease or does not decrease significantly.

4 Claims, 6 Drawing Sheets

USE OF TYROSOL AS A PHYSIOLOGICAL ENHANCER OF CREATINE AND ITS APPLICATION IN CONTINUOUS HIGH INTENSITY EXERCISE

CROSS-REFERENCE TO RELATED APPLICATIONS

The application claims priority to Chinese patent application No. 2024114720622, filed on Oct. 21, 2024, the entire contents of which are incorporated herein by reference.

TECHNICAL FIELD

The present invention relates to the field of sports nutrition supplements, particularly to the application of tyrosol as an enhancer of the physiological effects of creatine and its use in continuous high-intensity exercise.

BACKGROUND

Creatine, a nitrogen-containing organic acid, assists in providing energy to muscle and nerve cells. It is commonly added to various sports supplements, primarily for storing phosphocreatine in muscle tissues. Under the action of creatine kinase, creatine can be converted into phosphocreatine in the body. When the body requires adenosine triphosphate (ATP), phosphocreatine can be rapidly mobilized and used to produce ATP under the action of creatine kinase. The levels and resynthesis capacity of phosphocreatine greatly influence the muscle strength output.

The ATP and phosphocreatine stored in muscles serve as the initial energy sources mobilized during exercise, typically depleting within the first few seconds of muscle contraction. Subsequently, glycolysis or mitochondrial aerobic respiration becomes the primary energy supply source. Due to the rapid energy provision by phosphocreatine, it plays a critical role in explosive activities such as weightlifting and sprinting. Numerous studies have confirmed that creatine supplementation can enhance strength and improve performance in explosive exercises. Consequently, athletes and some fitness enthusiasts now opt to supplement with creatine to increase intramuscular phosphocreatine levels, thereby boosting the explosive power of muscle contractions. However, research also indicates that creatine supplementation primarily increases strength and explosive power, but does not significantly improve endurance. Due to the rapid depletion of phosphocreatine, even long-term creatine supplementation results in considerable strength decline post-resistance training. Continuous high-intensity exercise further accelerates the loss of strength gains brought by creatine. This suggests that creatine supplementation cannot sustain high levels of muscle strength during prolonged exercise. Multiple short-interval high-intensity exercises are very common in many sports competitions and regular training, necessary for achieving good performance. Despite this, creatine remains favored in the sports field, but there is a need for other methods or substances to fill its gap, especially for continuous high-intensity exercise performance.

SUMMARY

The purpose of the present invention is to address the shortcomings of existing technology by providing the application of tyrosol and/or tyrosol derivatives as physiological effect enhancers for creatine and/or creatine derivatives.

Furthermore, the tyrosol and/or tyrosol derivatives include salts, esters, acids, ketones, polymers, co-crystals, chelates, complexes, glycosides, hydrates, and substances formed by non-chemical bonding with other substances. Tyrosol derivatives are digested or metabolized in the body to form tyrosol, or they perform the same or similar physiological functions as tyrosol.

Furthermore, the creatine and/or creatine derivatives include salts, esters, ketones, hydrates, polymers, co-crystals, chelates, complexes, glycosides, and substances formed by non-chemical bonding with other substances, for example, creatine ethyl ester, phosphocreatine, glycocyamine, creatine citrate, zinc magnesium creatine, alkaline creatine, creatine pyruvate, creatine hydrates (including, but not limited to creatine monohydrate), and creatine malate. Creatine derivatives are digested or metabolized in the body to form creatine, or perform the same or similar physiological functions as creatine.

Furthermore, tyrosol and/or tyrosol derivatives: 20 mg to 3 g, creatine and/or creatine derivatives: 500 mg to 10 g; or the amount of tyrosol derivatives is equivalent to 20 mg-3 g of tyrosol based on molar conversion. Tyrosol and tyrosol derivatives: 20 mg to 3 g, should be understood as the total amount of tyrosol and tyrosol derivatives being 20 mg to 3 g; or the amount of creatine derivatives is equivalent to 500 mg-10 g of creatine based on molar conversion. Creatine and creatine derivatives: 500 mg to 10 g, should be understood as the total amount of creatine and creatine derivatives being 500 mg to 10 g.

The enhanced physiological effects include, but are not limited to, improves muscle endurance, reduces decline in muscle strength, enhances utilization of creatine by muscles; tyrosol stimulates the endurance-enhancing effects of creatine, reduces the decline of endurance levels; accelerates resynthesis of phosphocreatine, increases levels of phosphocreatine; improves resistance performance and endurance exercise performance. Especially, muscle endurance does not decline, or does not significantly decline, after continuous high-intensity exercise.

The present invention also provides a composition comprising tyrosol and/or tyrosol derivatives: 20 mg to 3 g, creatine and/or creatine derivatives: 500 mg to 10 g.

Or the amount of tyrosol derivatives is equivalent to 20 mg-3 g of tyrosol based on molar conversion. Tyrosol and tyrosol derivatives: 20 mg to 3 g, should be understood as the total amount of tyrosol and tyrosol derivatives being 20 mg to 3 g; or the amount of creatine derivatives is equivalent to 500 mg-10 g of creatine based on molar conversion. Creatine and creatine derivatives: 500 mg to 10 g, should be understood as the total amount of creatine and creatine derivatives being 500 mg to 10 g.

The product of the composition described in the present invention can be in various dosage forms, including but not limited to common pharmaceutical forms such as powders, suppositories, gels, oral solutions, hard capsules, and soft capsules. It can also be in common forms of health foods and dietary supplements such as beverages, solid beverages, soft drinks, hard capsules, soft capsules, multi-layer hard capsules, melt-in-mouth tablets, freeze-dried powders, milk tablets, chocolates, gummies, filled gummies, filled chocolates, tea beverages, and cold brew coffee.

The present invention also provides the application of tyrosol and/or tyrosol derivatives as physiological effect enhancers for creatine and/or creatine derivatives in continuous high-intensity exercise. Furthermore, the tyrosol and/or tyrosol derivatives include salts, esters, acids, ketones, polymers, co-crystals, chelates, complexes, glycosides, hydrates, and substances formed by non-chemical bonding with other substances. Tyrosol derivatives are digested or metabolized in the body to form tyrosol, or perform the same or similar physiological functions as tyrosol.

Furthermore, the creatine and/or creatine derivatives include salts, esters, ketones, hydrates, polymers, co-crystals, chelates, complexes, glycosides, and substances formed by non-chemical bonding with other substances, for example, creatine ethyl ester, phosphocreatine, glycocyamine, creatine citrate, zinc magnesium creatine, alkaline creatine, creatine pyruvate, creatine hydrates (including, but not limited to creatine monohydrate), and creatine malate. Creatine derivatives are digested or metabolized in the body to form creatine, or perform the same or similar physiological functions as creatine.

Furthermore, tyrosol and/or tyrosol derivatives: 20 mg to 3 g, creatine and/or creatine derivatives: 500 mg to 10 g; or the amount of tyrosol derivatives is equivalent to 20 mg-3 g of tyrosol based on molar conversion. Tyrosol and tyrosol derivatives: 20 mg to 3 g, should be understood as the total amount of tyrosol and tyrosol derivatives being 20 mg to 3 g; or the amount of creatine derivatives is equivalent to 500 mg-10 g of creatine based on molar conversion. Creatine and creatine derivatives: 500 mg to 10 g, should be understood as the total amount of creatine and creatine derivatives being 500 mg to 10 g.

Furthermore, continuous high-intensity exercise refers to the interval between high-intensity exercise 1 h, 5 h, 10 h, one day, two days, three days, etc., for many times of high-intensity exercise, such as 2, 3, 4, 5, 6, 7, 8, 9, 10 sessions, etc.

The enhanced physiological effects include, but are not limited to, improves muscle endurance, reduces decline in muscle strength, enhances utilization of creatine by muscles; tyrosol stimulates the endurance-enhancing effects of creatine, reduces the decline of endurance levels; accelerates resynthesis of phosphocreatine, increases levels of phosphocreatine; improves resistance performance and endurance exercise performance. Especially, muscle endurance does not decline, or does not significantly decline, after continuous high-intensity exercise.

DETAILED DESCRIPTION OF THE EMBODIMENTS

Figure 1:
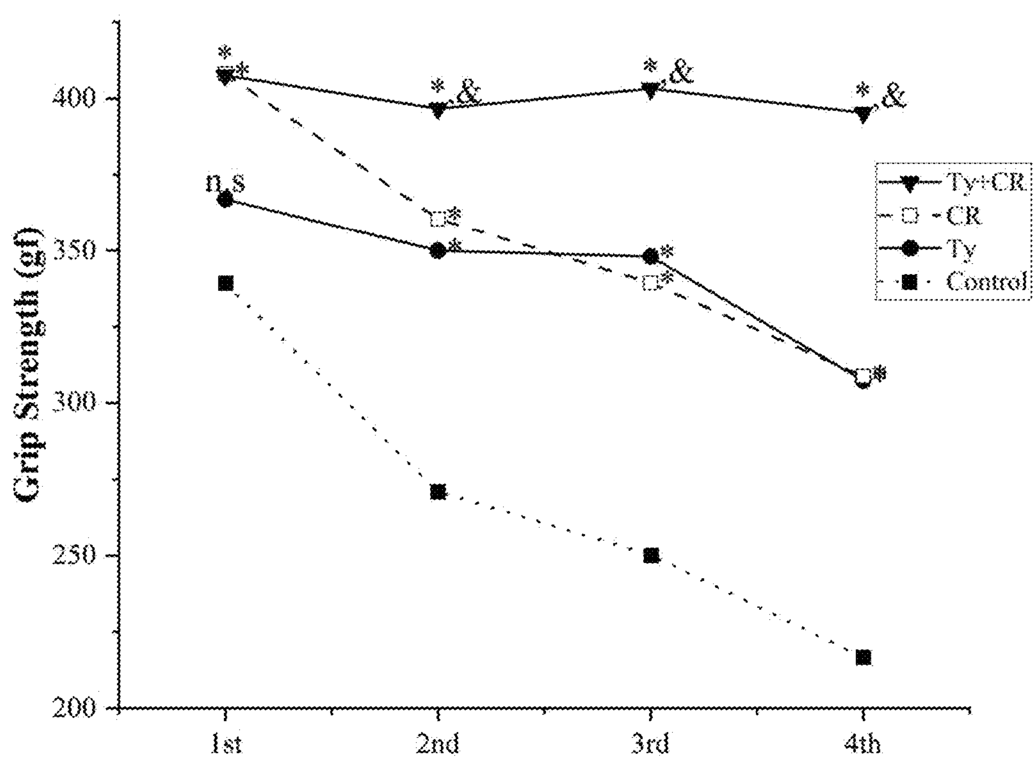
FIG. 1: The trend in grip strength of mice.

To facilitate the understanding of those skilled in the art, the invention is further illustrated below in conjunction with embodiments. The content mentioned in the embodiments is not intended to limit the invention.

Example 1

The application of tyrosol as a physiological effect enhancer for creatine.

Tyrosol and/or tyrosol derivatives: 20 mg, creatine and/or creatine derivatives: 10 g.

Example 2

The application of tyrosol as a physiological effect enhancer for creatine.

Tyrosol and/or tyrosol derivatives: 3 g, creatine and/or creatine derivatives: 500 mg.

Example 3

The application of tyrosol as a physiological effect enhancer for creatine.

Tyrosol and/or tyrosol derivatives: 1 g, creatine and/or creatine derivatives: 2 g.

Example 4

The application of tyrosol as a physiological effect enhancer for creatine in continuous high-intensity exercise.

Tyrosol and/or tyrosol derivatives: 20 mg, creatine and/or creatine derivatives: 10 g.

Example 5

The application of tyrosol as a physiological effect enhancer for creatine in continuous high-intensity exercise.

Tyrosol and/or tyrosol derivatives: 3 g, creatine and/or creatine derivatives: 500 mg.

Example 6

The application of tyrosol as a physiological effect enhancer for creatine in continuous high-intensity exercise.

Tyrosol and/or tyrosol derivatives: 1 g, creatine and/or creatine derivatives: 2 g.

Example 7

The application of tyrosol as a physiological effect enhancer for creatine in continuous high-intensity exercise.

Tyrosol and/or tyrosol derivatives: 1 g, creatine and/or creatine derivatives: 2 g. Continuous high-intensity exercise refers to performing high-intensity exercise every other day.

Experiment 1 Tyrosol enhances creatine utilization

Animal Experiment: Thirty 8-week-old mice were prepared and acclimated to the laboratory environment for one week before being randomly divided into three groups. Control Group: Normal diet with no added active ingredients, serving as the control group. CR Group: Normal diet supplemented with 5% creatine monohydrate. Ty+CR Group: Normal diet supplemented with 1% tyrosol and 5% creatine monohydrate.

After two weeks of feeding, the mice were anesthetized, and the leg skeletal muscles were dissected, showing clear connective tissue without blood. For muscle contraction tests via electrical stimulation, the muscles were first incubated in a specific physiological buffer solution for 10 minutes to recover from dissection. The muscles were then clamped with aluminum forceps and stimulated using platinum electrodes and a capacitor alternating polarity discharge.

The muscles were subjected to 250 ms electrical stimulation with six intervals, each interval progressively shortened from 4 s to 1 s. After six interval stimulations, a 1-minute observation period followed before the next round, totaling four rounds. The left and right leg muscles of each mouse were labeled, and subjected to the aforementioned electrical stimulation test.

Phosphocreatine (PCr) and creatine (CR) levels were immediately measured in the dissected right leg muscles after the electrical stimulation test. The dissected left leg muscles of all groups were measured for phosphocreatine and creatine levels 5 minutes after the test. Total creatine (TCr) levels were the sum of phosphocreatine and creatine levels. Standard fluorescence assay was used to determine phosphocreatine and creatine levels in muscle samples extracted with perchloric acid precipitation.

TABLE 1

Changes of phosphocreatine, creatine and total creatine levels in skeletal muscle of mice in each group after continuous interval stimulation.

| Groups | | Creatine (CR) | Phosphocreatine (PCr) | Total creatine (TCr) |
|---|---|---|---|---|
| Immediately | Control | 41.3 ± 4.6 | 10.1 ± 2.6 | 51.4 ± 4.8 |
| | CR | 49.2 ± 3.7 | 13.4 ± 1.2 | 62.6 ± 4.0 |
| | Ty + CR | 51.2 ± 3.5 | 19.2 ± 1.8 | 70.4 ± 4.2 |
| 5 min later | Control | 20.6 ± 3.2 | 31.8 ± 3.6 | 52.4 ± 3.6 |
| | CR | 22.7 ± 2.8 | 39.7 ± 2.2 | 62.4 ± 3.0 |
| | Ty + CR | 23.4 ± 2.7 | 46.8 ± 2.5 | 70.2 ± 2.8 |

Note: Values are expressed as mean±SE, in mmol/kg dry weight.

As shown in Table 1, the levels of creatine, phosphocreatine, and total creatine in both the CR group and the Ty+CR group were higher than those in the control group, regardless of whether the measurements were taken immediately after stimulation or 5 minutes later. This indicates that pre-administration of creatine monohydrate or a combination of creatine monohydrate and tyrosol significantly increases the levels of creatine and phosphocreatine in the skeletal muscles of mice. Additionally, the Ty+CR group exhibited higher levels across all three indicators compared to the CR group, suggesting that the combined supplementation of creatine and tyrosol can further enhance creatine and phosphocreatine levels, providing greater energy supply to the muscles.

The data in the table also shows that the total creatine levels remained almost unchanged in each group, whether measured immediately after stimulation or 5 minutes later. However, the creatine levels significantly decreased after a 5-minute recovery period in each group, while phosphocreatine levels significantly increased. This indicates that during muscle contraction induced by electrical stimulation, a large amount of phosphocreatine is consumed by the working muscles. After muscle contraction ends, the stored creatine rapidly converts into phosphocreatine to replenish the phosphocreatine stores, since the "pool" size (total creatine levels) remains unchanged. Therefore, enhancing the energy supply from phosphocreatine focuses on accelerating the conversion of creatine and enhancing its utilization.

By comparing the "immediate" data with the "5-min-later" data within each group, we were surprised to find that 5 minutes after the end of muscle contraction induced by electrical stimulation, the creatine levels in the control group decreased by 50.12%, in the CR group by 53.86%, and in the Ty+CR group by 54.3%. This indicates that the Ty+CR group had the highest creatine conversion rate, demonstrating that the addition of tyrosol enhances the utilization of creatine in the body.

Experiment 2 Tyrosol maintains the high level of muscle strength brought by creatine.

Animal Experiment 1: Six-week-old mice were used. After one week of acclimation to the environment, the mice were randomly divided into the following groups:

Control Group: Normal diet, serving as the control group.

Ty Group: Normal diet, with 75 mg/kg tyrosol administered by gavage daily.

CR Group: Normal diet, with 260 mg/kg creatine monohydrate administered by gavage daily.

Ty+CR Group: Normal diet, with 75 mg/kg tyrosol+260 mg/kg creatine monohydrate administered by gavage daily.

This regimen continued for 4 weeks. The first grip strength test was conducted 30 minutes after the last gavage. The grip strength of the mice's limbs was measured using a grip strength meter. After a 1-hour rest, the mice underwent the first exhaustive swimming exercise. Each mouse had a tin wire weighing 5% of its body weight and a detector attached to its tail. The mice were then placed in a weighted swimming tank at a water temperature of 30±1° C. for the exhaustive swimming test. Exhaustion was considered if the mice touched the bottom of the tank three consecutive times within 30 seconds. The detector recorded the mice's bottom-touching instances, and upon determining exhaustion, the swimming tank automatically lifted the mice, recording the exhaustive swimming time.

24 hours after the first swimming exercise, the second grip strength test and exhaustive swimming exercise were conducted using the same methods, recording grip strength data and exhaustive swimming time. The third and fourth grip strength tests and exhaustive swimming exercises were conducted 24 hours after the previous exercise, recording the respective data. The gavage regimen remained unchanged during the intervals.

FIG. 1: * indicates significance compared to the Control Group, & indicates significance compared to the Creatine and Tyrosol Groups, and n.s indicates no significance compared to the Control Group.

As shown in FIG. 1, the muscle strength (grip strength) of mice in the creatine group (CR) and the tyrosol+creatine group (Ty+CR) was significantly increased compared to the control group, while the mice in the tyrosol group (Ty) did not show a significant increase in muscle strength (the first grip strength data was not significantly different from the control group). In subsequent exercises, the muscle strength of the control group mice decreased rapidly, and as expected, the decline rate in the creatine group was also rapid. However, surprisingly, the muscle strength of the mice in the tyrosol+creatine group remained stable at the high initial level during continuous high-intensity exercise, showing almost no decline and consistently remaining significantly higher than the control group. From the second exercise onward, the rapid decline in muscle strength in the creatine group caused a significant difference in grip strength values between the creatine group and the tyrosol+creatine group. Even though tyrosol supplementation alone did not significantly improve muscle strength in mice, and despite the rapid consumption characteristics of creatine itself, the simultaneous supplementation of both produced unexpected effects, robustly reversing the decline in muscle strength. This indicates that tyrosol can maintain the enhancement effect of creatine on muscle strength during continuous exercise, specifically preserving the improvement of resistance exercise performance attributed to creatine. This could be due to tyrosol promoting the utilization of creatine in the body and accelerating the resynthesis of phosphocreatine, consistent with Experiment 1.

Figure 2:
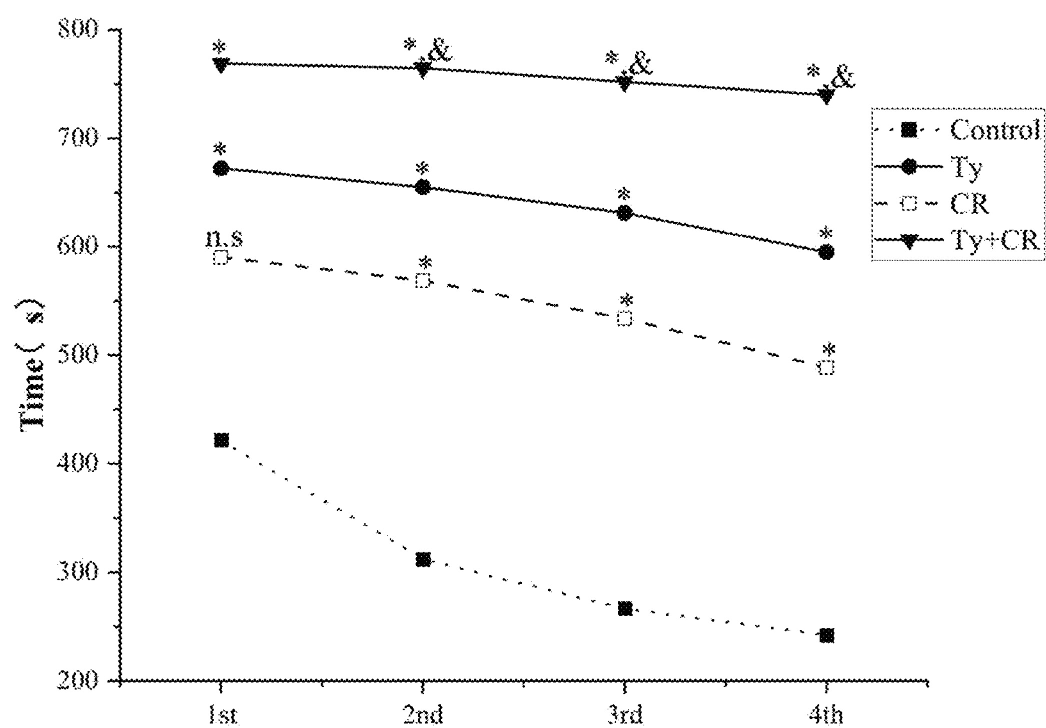
FIG. 2: The trend in exhaustive swimming time of each group of mice.

FIG. 2: * indicates significance compared to the Control Group, & indicates significance compared to the Creatine Group, and n.s indicates no significance compared to the Control Group.

As shown in FIG. 2, the exercise time of the mice in the tyrosol group and the tyrosol+creatine group is significantly higher than that of the control group mice. The creatine group did not improve the endurance of the mice at the beginning (the first exercise time was not significantly different from the control group). Significant differences between the creatine group and control group appeared only after the control group's exercise time significantly decreased in subsequent exercises. The endurance enhancement in the tyrosol+creatine group consistently remained high. We were surprised to find that during continuous exercise, the exercise time of the other three groups (control, tyrosol, creatine groups) declined to varying degrees, while the exercise time of the tyrosol+creatine group decreased so slowly that it was negligible. This is consistent with the trend observed in the grip strength test. This indicates that tyrosol stimulates the endurance-enhancing effects of creatine, and simultaneous supplementation of tyrosol and creatine not only maintains high levels of resistance exercise performance during continuous exercise but also sustains high levels of endurance exercise performance.

TABLE 2

Percentage change of muscle strength in each group of mice during and after continuous high-intensity exercise

| | Control | Ty | CR | Ty + CR |
|---|---|---|---|---|
| First exercise | 1 | 1 | 1 | 1 |
| Second exercise | 80.65% | 97.40% | 89.24% | 97.52% |
| Third exercise | 74.51% | 96.55% | 83.81% | 98.94% |
| Fourth exercise | 64.40% | 85.05% | 76.10% | 97.04% |

Note: The data compared each group's grip strength in subsequent exercises to their grip strength in the first exercise, reflected the difference in grip strength from the initial value.

As shown in Table 2, the grip strength values of mice in each group were highest during the first exercise. The muscle strength of the mice in the control group, tyrosol group, and creatine group all declined to varying degrees in subsequent exercises. In contrast, the muscle strength of the mice in the tyrosol+creatine group showed almost no decline, maintaining over 97% of the high initial muscle strength level during continuous high-intensity exercise.

TABLE 3

Percentage change of exhaustive exercise time in each group of mice during and after continuous high-intensity exercise.

| | Control | Ty | CR | Ty + CR |
|---|---|---|---|---|
| First exercise | 1 | 1 | 1 | 1 |
| Second exercise | 75.08% | 97.13% | 95.26% | 99.56% |
| Third exercise | 64.26% | 94.54% | 88.10% | 98.22% |
| Fourth exercise | 58.71% | 88.45% | 81.88% | 96.46% |

Note: The data compared each group's exhaustive exercise time in subsequent exercises to their exhaustive exercise time in the first exercise, reflected the difference in exhaustive exercise time from the initial value.

As shown in Table 3, the exercise time of mice in each group was highest during the first exercise. The exercise time of the mice in the control group, tyrosol group, and creatine group all declined to varying degrees in subsequent exercises. In contrast, the endurance of the mice in the tyrosol+creatine group showed almost no decline, maintaining over 96% of the high endurance performance level observed in the first swimming exercise during continuous high-intensity exercise.

Experiment 3 Tyrosol Maintains the High Level of Muscle Strength Brought by Creatine Animal Experiment 2: Six-week-old mice were used. After one week of acclimation to the environment, the mice were randomly divided into the following groups:

Control Group: Normal diet, serving as the control group.

Ty 1 Group: Normal diet, with 2.6 mg/kg tyrosol administered by gavage daily.

CR 1-3 Groups: Normal diet, with 65 mg/kg, 390 mg/kg, and 1300 mg/kg creatine monohydrate administered by gavage daily.

Ty+CR 1-4 Groups: Normal diet, with 2.6 mg/kg tyrosol+65 mg/kg creatine monohydrate, 130 mg/kg tyrosol+130 mg/kg creatine monohydrate, 390 mg/kg tyrosol+1300 mg/kg creatine monohydrate, and 2.6 mg/kg tyrosol+1300 mg/kg creatine monohydrate administered by gavage daily.

With the exception of groups Ty 1, CR 1, and Ty+CR 1 which were fed for 8 weeks, all other dosing groups were fed for 4 weeks, with one daily gavage. Groups CR 3, Ty+CR 3, and Ty+CR 4 received their daily gavage dose in two separate administrations each day. Half of the control group was fed for 4 weeks, and the other half for 8 weeks. The first grip strength test was conducted 30 minutes after the last gavage, followed by the first exhaustive swimming exercise after a 1-hour rest. Grip strength and swimming exercise methods were the same as previously described. 24 hours after the first swimming exercise, the second grip strength test and exhaustive swimming exercise were conducted using the same methods, recording grip strength data and exhaustive swimming time. The third and fourth grip strength tests and exhaustive swimming exercises were conducted 24 hours after the previous exhaustive swimming exercise, recording grip strength data and exhaustive swimming time. Groups CR 3 and Ty+CR 4 underwent up to the eighth grip strength test and exhaustive swimming exercise, maintaining the same exercise methods. During the intervals, the gavage regimen for each group remained unchanged.

Figure 3:
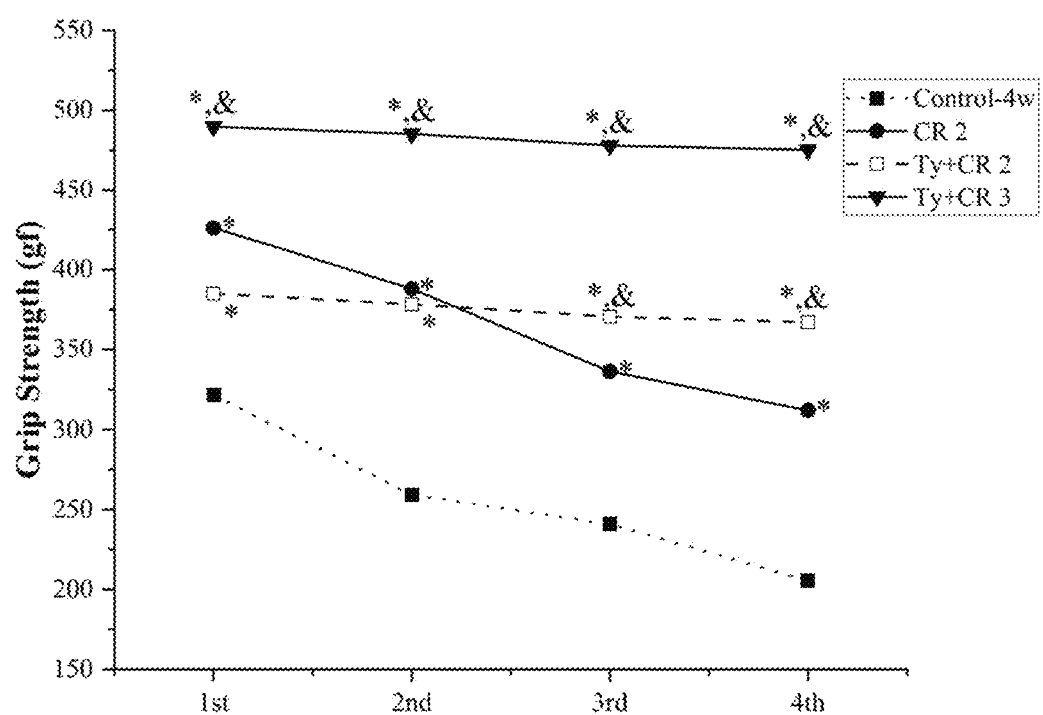
FIG. 3: The trend in grip strength of each group of mice.

FIG. 3: * indicates significance compared to the Control Group, & indicates significance compared to the Creatine Group.

As shown in FIG. 3, the muscle strength of the mice in the creatine group and the two tyrosol+creatine groups were significantly higher than that in the control group. Consistent with the results of the above experiments, the muscle strength of the mice in the two tyrosol+creatine groups remained almost unchanged during continuous exercise. Moreover, we were surprised to find that even though the creatine dose in the tyrosol+creatine group (Ty+CR 2) was one-third of that in the creatine group (CR 2), the muscle strength of the mice in the Ty+CR 2 group still maintained the level of the first grip strength test. The grip strength values of Ty+CR 2 group in the third and fourth tests were significantly higher than those in the CR 2 group due to the marked decline in muscle strength of the mice in the CR 2 group. In the other tyrosol+creatine group (Ty+CR 3), both the tyrosol and creatine doses were increased, consequently, this group exhibited the highest grip strength values from the beginning and consistently maintained the initial high level of muscle strength during continuous exercise.

Figure 4:
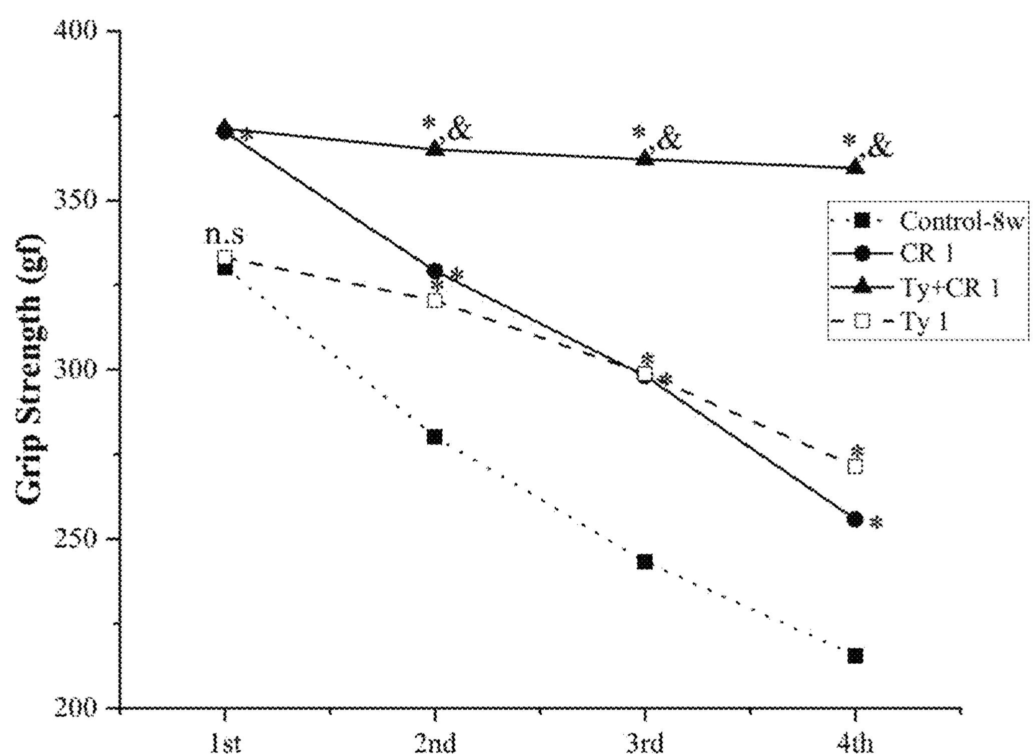
FIG. 4: The trend in grip strength of each group of mice administered a low dose of tyrosol.

FIG. 4: * indicates significance compared to the Control Group, & indicates significance compared to the Creatine Group and the Tyrosol Group, and n.s indicates no significance compared to the Control Group.

As shown in FIG. 4, the low-dose creatine group (CR 1) and the low-dose tyrosol+creatine group (Ty+CR 1) still significantly increased the muscle strength of the mice, although the extent of improvement was not high. The tyrosol+creatine group continued the aforementioned trend, maintaining the initial high level of muscle strength in mice during continuous exercise.

Figure 5:
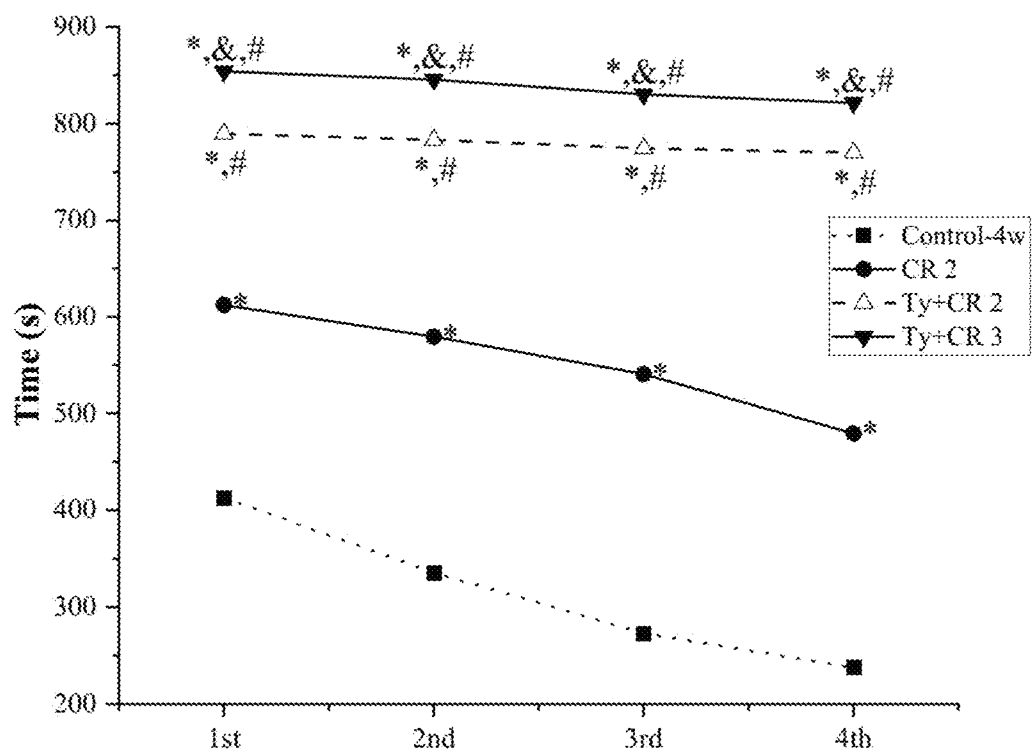
FIG. 5: The trend in exhaustive swimming time of each group of mice.

FIG. 5: * indicates significance compared to the Control Group, #indicates significance compared to the Creatine Group, and & indicates significance compared to the Ty+CR 2 Group.

As shown in FIG. 5, although the high-dose creatine group (CR 2) was able to enhance the endurance of mice and prolong exercise time, its effect on endurance was not as strong as its effect on grip strength. In contrast, the tyrosol+creatine group (Ty+CR 2), supplemented with the same proportion of tyrosol and creatine, showed significantly higher endurance in mice compared to the high-dose CR 2 group. This indicates that tyrosol compensates for the weaker endurance enhancement of creatine. Moreover, the higher the dose (Ty+CR 3), the greater the improvement in endurance.

Figure 6:
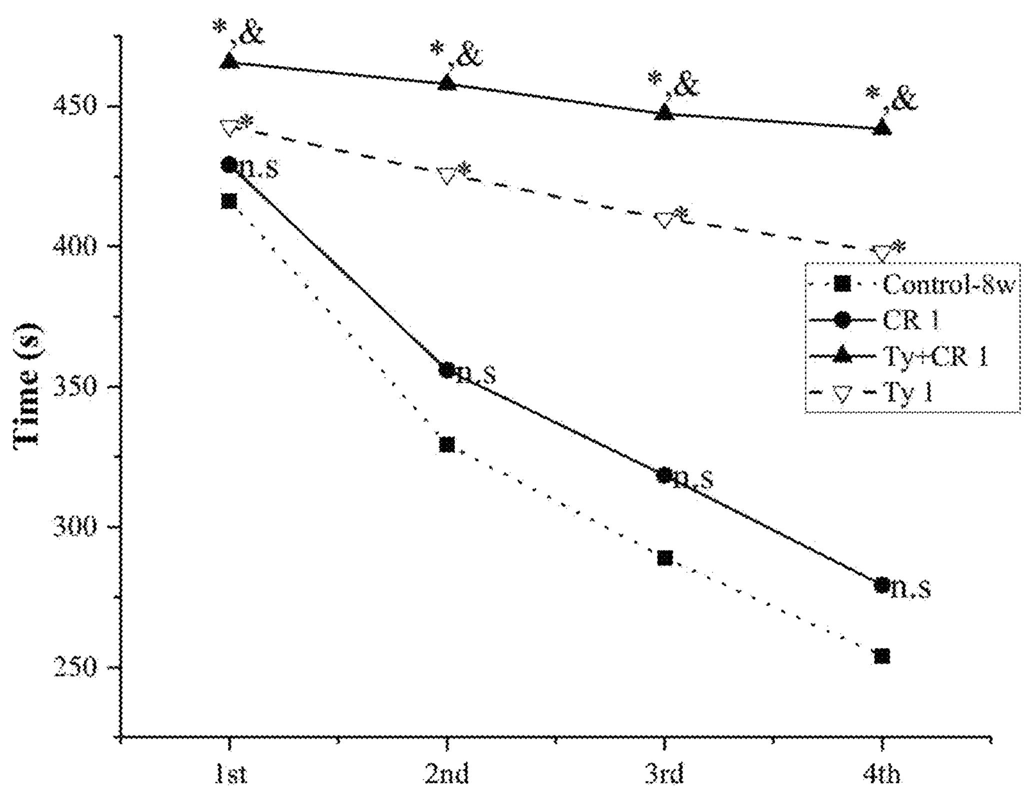
FIG. 6: The trend in exhaustive swimming time of each group of mice administered a low dose of tyrosol.

FIG. 6: * indicates significance compared to the Control Group, & indicates significance compared to the Creatine Group and the Tyrosol Group, and n.s indicates no significance compared to the Control Group.

As shown in FIG. 6, the low-dose creatine group (CR 1) did not improve the endurance time of mice, showing no significant difference from the control group throughout continuous exercise. This highlights the limitation of creatine in enhancing endurance. However, the simultaneous supplementation of low-dose tyrosol significantly improved the endurance of mice (Ty+CR 1), and the endurance improvement was higher than that of the same-dose tyrosol group (Ty 1) alone. The exercise time in the Ty+CR 1 group was significantly higher than in the Ty 1 group (Ty+CR 1 vs. Ty 1, significant difference). This indicates that the presence of tyrosol stimulates the endurance-enhancing effect of creatine. Even though low-dose creatine alone cannot improve endurance, the combined use of creatine and tyrosol showed unexpected results, with the combination significantly enhancing endurance more than tyrosol alone.

In the comparison of the experimental results of CR 3 (1300 mg/kg creatine) and Ty+CR 4 (2.6 mg/kg tyrosol+1300 mg/kg creatine), it is evident that in the grip strength tests of mice, the grip strength data for the two groups from the first to the sixth exercise were almost identical, with no significant difference. Both groups showed a decline in muscle strength as the number of exercises increased, which could be due to the dominant creatine content in the composition, resulting in no difference between the composition group and the creatine group during the first six exercises. However, unexpectedly, during the seventh and eighth exercises, the grip strength values of the composition group were significantly higher than those of the creatine group. Although both groups still experienced a decline in muscle strength, the decline was slower in the composition group, thereby creating a gap with the creatine group. This indicates that the small amount of tyrosol in the composition plays a role in maintaining the muscle strength enhancement brought by creatine during long-term continuous exercise, reducing the decline in muscle strength.

We subjected each group of mice to four consecutive intermittent grip strength tests and exhaustive exercises. The results of the first exercise test showed that the muscle strength of the mice supplemented with tyrosol alone did not increase. The muscle strength of the mice supplemented with creatine and those supplemented with both tyrosol and creatine significantly increased as expected. However, in the subsequent second, third, and fourth continuous high-intensity exercises, we were surprised to find that the muscle strength of the mice in the normal control group, tyrosol group, and creatine group all significantly declined, with the rate of decline increasing. Conversely, the muscle strength of the mice supplemented with both tyrosol and creatine remained almost unchanged from the initial level, indicating a synergistic effect of tyrosol and creatine in enhancing and maintaining muscle strength without decline.

Furthermore, the results of the exhaustive exercise time showed the same trend. The exercise time of the mice supplemented with both tyrosol and creatine was significantly higher than that of the mice in the creatine group from the first exercise, indicating that tyrosol not only maintained the resistance performance of creatine during continuous exercise but also greatly compensated for creatine's relatively weaker effect on endurance improvement.

The above experimental results indicate that the supplementation of tyrosol enhances cellular utilization of creatine and promotes the resynthesis of phosphocreatine. While tyrosol supplementation alone does not increase muscle strength, the addition of tyrosol allows creatine to maintain an initial high level of muscle strength during exercise, reversing the reduction in muscle strength caused by high-intensity exercise. This demonstrates a synergistic effect between tyrosol and creatine. Furthermore, the addition of tyrosol also stimulates the endurance-enhancing effects of creatine. Combined supplementation of creatine and tyrosol not only enhances endurance performance but also improves resistance exercise performance.

U.S. Pat. No. 9,446,006B2 discloses a composition containing hydroxytyrosol or olive juice containing hydroxytyrosol in combination with at least one of the following compounds: creatine, coenzyme Q10, resveratrol, caffeine, L-carnitine, B vitamins (B1, B2, B3, B5, B6, and/or B12), and ginseng (preferably root) extract. This composition can be used to maintain or increase mitochondrial biogenesis in myocardial, skeletal muscle, and liver tissues. The invention claims that these compositions synergistically enhance the body's ability to produce energy and/or increase cellular energy production. It also relates to pharmaceutical and nutraceutical compositions for conditions characterized by altered mitochondrial function and biogenesis, such as cardiac strength, various liver diseases, improved muscle/fat ratio, and muscle endurance. The specification states that the benefits of the composition include at least one of the following (excerpting the first four here): helps promote endurance, helps promote recovery after exercise, helps reduce muscle fatigue, helps reduce muscle soreness.

In this patent, hydroxytyrosol is introduced as an ingredient with a positive cardiovascular protective effect, with anti-atherosclerotic properties. Subsequent example data demonstrate that hydroxytyrosol can promote mitochondrial function. The patent mentions creatine primarily for its characteristic of enhancing energy supply. For making more ATP and making it available for the body (physical energy, endurance, muscle force), creatine transports the energy generated in form of ATP to the myofibers in usable form (creatine phosphate).

Unlike our invention, this patent primarily selects compositions based on enhanced mitochondrial function. The example data presented focus on the synergistic effects of hydroxytyrosol and other ingredients (only caffeine and L-carnitine) on mitochondrial activity and biogenesis, as well as mitochondrial energy production. Its specification does not propose the maintenance effect of hydroxytyrosol or tyrosol on muscle strength during continuous exercise when supplemented with creatine, nor does it suggest that hydroxytyrosol or tyrosol can stimulate creatine's endurance-enhancing effects or enhance the body's or cells' conversion and utilization of creatine. Our invention primarily explores the deeper synergistic effects between tyrosol and creatine. In contrast, this patent utilizes the characteristic of creatine to promote ATP production, proposing that the combination of hydroxytyrosol and creatine may enhance mitochondrial function and synergistically promote energy production, resulting in a series of exercise benefits based on improved mitochondrial function. This proposition is only a rough conceptual description without specific supporting research data, which we believe does not predict the technical effects of our invention.

Referring to the "Equivalent Dose Ratio by Body Surface Area Between Humans and Animals", the daily human equivalent dose for each substance used in the mouse experiments is calculated as follows:

TABLE 4

Euivalent dose for mice and humans

| | Mice dose | Adult equivalent dose |
|---|---|---|
| Tyrosol | 2.6 mg/kg | 20 mg |
| | 75 mg/kg | 576 mg |
| | 130 mg/kg | 1 g |
| | 390 mg/kg | 3 g |
| Creatine | 65 mg/kg | 500 mg |
| | 130 mg/kg | 1 g |
| | 260 mg/kg | 2 g |
| | 390 mg/kg | 3 g |
| | 1300 mg/kg | 10 g |

It is to be understood by those skilled in the art that, unless otherwise defined, all terms used herein (including technical and scientific terms) have the same meaning as commonly understood by one of ordinary skill in the art to which this invention belongs. It is also to be understood that terms, such as those defined in commonly used dictionaries, should be interpreted as having a meaning consistent with their meaning in the context of the relevant art and should not be interpreted in an idealized or overly formal sense unless expressly so defined herein.

It should be understood that the detailed description of the technical solutions of the present invention provided above with reference to the preferred embodiments is illustrative and not limiting. Those skilled in the art, upon reading the specification, may make modifications to the technical solutions described in the embodiments, or make equivalent replacements of some of the technical features; such modifications or replacements do not depart from the spirit and scope of the technical solutions of the respective embodiments of the present invention.

What is claimed is:

1. An application of tyrosol and/or tyrosol derivatives as physiological effect enhancers for creatine and/or creatine derivatives; wherein the one or more enhanced physiological effects selected from the group consisting of improving muscle endurance, reducing decline in muscle strength, enhancing utilization of creatine by muscles; tyrosyl stimulating the endurance-enhancing effects of creatine, reducing the decline of endurance levels; accelerating resynthesis of phosphocreatine, increasing levels of phosphocreatine; improving resistance performance and endurance exercise performance; the muscle endurance does not significantly decline, after continuous high-intensity exercise: wherein the tyrosol and/or the tyrosyl derivatives include salts, esters, acids, ketones, polymers, co-crystals, chelates, complexes, glycosides, hydrates, and substances formed by non-chemical bonding with other substances; and/or creatine and/or creatine derivatives include salts, esters, ketones, hydrates, polymers, co-crystals, chelates, complexes, glycosides, and substances formed by non-chemical bonding with other substances.

2. The application according to claim 1, wherein the amount of tyrosol and/or tyrosol derivatives is 20 mg to 3 g, and the amount of creatine and/or creatine derivatives is 500 mg to 10 g; or the amount of tyrosol derivatives is equivalent to 20 mg-3 g of tyrosol based on molar conversion; or the amount of creatine derivatives is equivalent to 500 mg-10 g of creatine based on molar conversion.

3. A composition, wherein comprising tyrosol and/or tyrosol derivatives: 20 mg to 3 g, creatine and/or creatine derivatives: 500 mg to 10 g; or the amount of tyrosol derivatives is equivalent to 20 mg-3 g of tyrosol based on molar conversion; or the amount of creatine derivatives is equivalent to 500 mg-10 g of creatine based on molar conversion; wherein the tyrosol and/or tyrosyl derivatives include salts, esters, acids, ketones, polymers, co-crystals, chelates, complexes, glycosides, hydrates, and substances formed by non-chemical bonding with other substances; and/or the creatine and/or creatine derivatives include salts, esters, ketones, hydrates, polymers, co-crystals, chelates, complexes, glycosides, and substances formed by non-chemical bonding with other substances.

4. The application according to claim 1, wherein continuous high-intensity exercise refers to the interval between high-intensity exercise 1 h, 5 h, 10 h, one day, two days, three days, etc., for many times of high-intensity exercise, such as 2, 3, 4, 5, 6, 7, 8, 9, 10 sessions, etc.

* * * * *